United States Patent [19]
Levin

[11] Patent Number: 5,991,648
[45] Date of Patent: Nov. 23, 1999

[54] ADJUSTABLE PULSE OXIMETRY SENSOR FOR PEDIATRIC USE

[75] Inventor: Paul Levin, Santa Cruz, Calif.

[73] Assignee: Palco Labs, Inc., Santa Cruz, Calif.

[21] Appl. No.: 09/050,864

[22] Filed: Mar. 30, 1998

[51] Int. Cl.⁶ .................................................... A61B 5/00
[52] U.S. Cl. ............................................................ 600/344
[58] Field of Search ................................... 600/309, 310, 600/322, 323, 340, 344; 602/66; 128/882, 893; 24/16 PB, 30.5 P

[56] References Cited

U.S. PATENT DOCUMENTS

| | | | |
|---|---|---|---|
| 4,770,175 | 9/1988 | McEwen | 600/203 |
| 5,437,275 | 8/1995 | Amundsen et al. | 600/323 |
| 5,615,540 | 4/1997 | Peterson et al. | 24/16 PB |

*Primary Examiner*—Eric F. Winakur

[57] ABSTRACT

A pulse oximetry sensor for use on pediatric patients comprised of a resilient foot wrap extending around the patient's foot, with an adjustable slide having slotted openings into which the ends of the foot wrap are inserted. The slide carries a plunger with a piercing member which can be pushed downward through the rubber to lock the slide in place making the foot wrap variable in size. The wrap has two resilient receptacles into which sensors are inserted, the receptacles being sized relative to the sensors so that the flexible receptacles stretch and securely hold the sensors in position.

4 Claims, 6 Drawing Sheets

ADJUSTABLE PULSE OXIMETRY SENSOR FOR PEDIATRIC USE

BACKGROUND AND SUMMARY OF THE INVENTION

Various sensors for pulse oximeters have been designed since oximetry came into common use in the early 1980s. Presently, about two-thirds of sensors used in the United States are of the disposable or single-use type. For example, the Goodman et al U.S. Pat. No. 4,830,014, assigned to Nellcor Incorporated, teaches emitter and detector elements of the sensor combined on al flexible strip, coated with adhesive, and then wrapped around a body part such as the finger or, in the case of babies, a foot. Since a disposable sensor at a minimum requires red and infrared light-emitting-diodes (LED), a photodetector and a shielded cable, disposable devices are a severe ongoing expense for the user.

Nellcor has developed a recycling program in which the sensor can be reused two or three times after being reconditioned at the factory; but, nevertheless, the cost for each patient use is not less than $7.00 and can be up to double that amount. Several attempts have been made by various companies to make some parts of the sensor more reusable so as to avoid the cost of replacing the entire device. For example, Swedlow et al of Nellcor have designed a sensor in which only the light emitters are discarded, the cable and detector portion being retained (U.S. Pat. No. 5,209,230).

Amundsen et al describe a reusable cable which is inserted into a tubular disposable finger cover made of paper or plastic which is designed to fit over a digit (U.S. Pat. No. 5,437,275).

Another attempt to avoid the cost of disposable sensors is that of Thomas et al (U.S. Pat. No. 5,170,786) whose group designed a probe using a disposable wrap with two square holes and a complimentary cable with sensing elements which plug into the holes in the fastening wrap. A flange surrounds the sensors and is an important element in stabilizing the detectors and emitters in this design. The sensors of this design project above the surface of the wrap. In practice, the wrap of this design relies on an adhesive coating for attachment to the skin and for stabilization of the sensing elements onto the wrap.

Pediatric sensors present the additional problem of the fragility of neonatal skin, especially if the infant is premature. Skin breakdown is a constant concern when sticky adhesive sensors are used in this very young patient population.

The present design advances the state-of-the-art since the cable and sensing elements are reusable and even the foot wrap which holds the sensing elements can be reused many times, making it very economical for the user. The present design does not require an adhesive for attachment to the skin or for stabilizing the sensors to the wrap. The wrap, itself, is made of very thin, semi-transparent rubberlike material, such as Kraton. The wrap is perforated to allow egress of perspiration and the perforations also assist in stabilization of the wrap around the foot.

The slight elasticity of the rubbery material helps it to conform to the infant's foot and gives just enough snugness to stabilize the sensor. The adjustable feature to be described permits easy adaptation to a range of pediatric foot sizes. Finally, the shape of the receptacles and their elasticity facilitates both insertion and removal of the sensing elements and stabilizes the emitters and photodetector during use.

A primary object of the invention is to provide an adjustable pulse oximetry sensor for pediatric use which is reusable and therefore cost effective.

A further object of the invention is to provide a pediatric pulse oximetry sensor which attaches to the patient's foot without requiring the use of adhesives.

A further object of the invention is to provide a reusable pulse oximetry sensor for pediatric use wherein the connecting cable, the sensing elements, and the foot wrap are all usable many times.

Another object of the invention is to provide a foot wrap for use in pediatric oximetry sensors which not only avoids the use of adhesive, but is also perforated to allow flow of perspiration.

Yet another object of the invention is to use resilient receptacles carried by the foot wrap and which are sized relative to the sensors so that the receptacles stretch to receive a sensor and resiliently grip and enclose the sensor to hold it securely in position.

Further, objects and advantages of the invention will become apparent from the following description and the drawings, wherein:

DETAILED DESCRIPTION OF THE DRAWINGS

Figure 1:
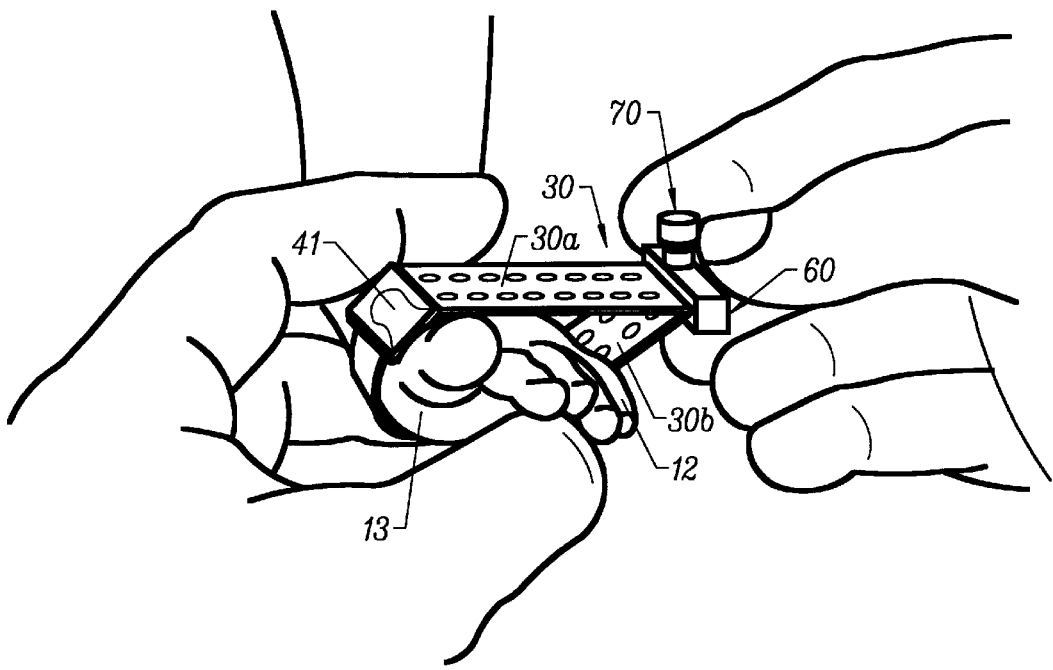
FIG. 1 is a perspective view of the foot wrap of the present invention being applied to the left foot of an infant patient.
Figure 2:
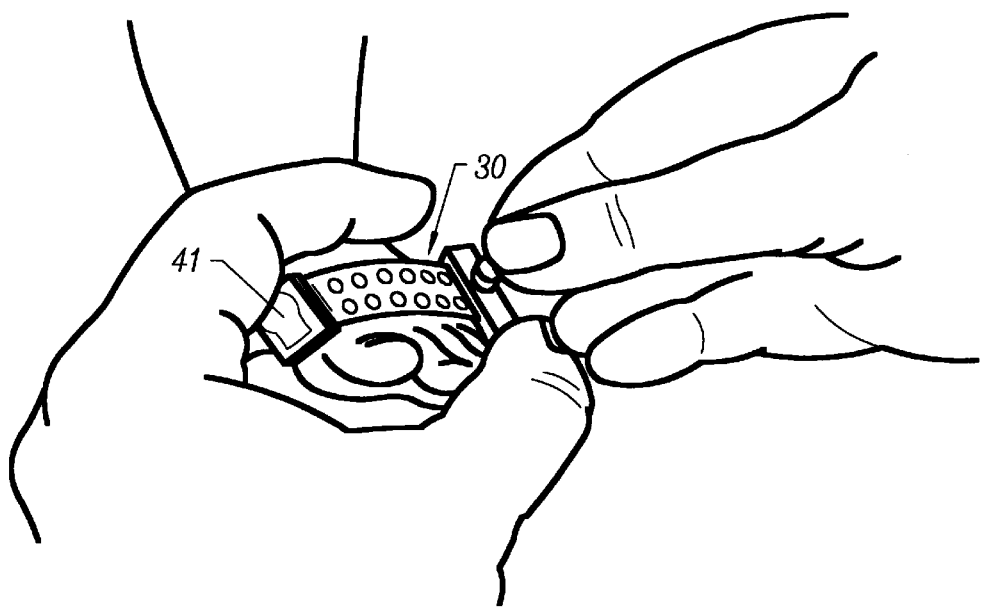
FIG. 2 shows the foot wrap of FIG. 1 after it has been tightened and locked in position.
Figure 3:
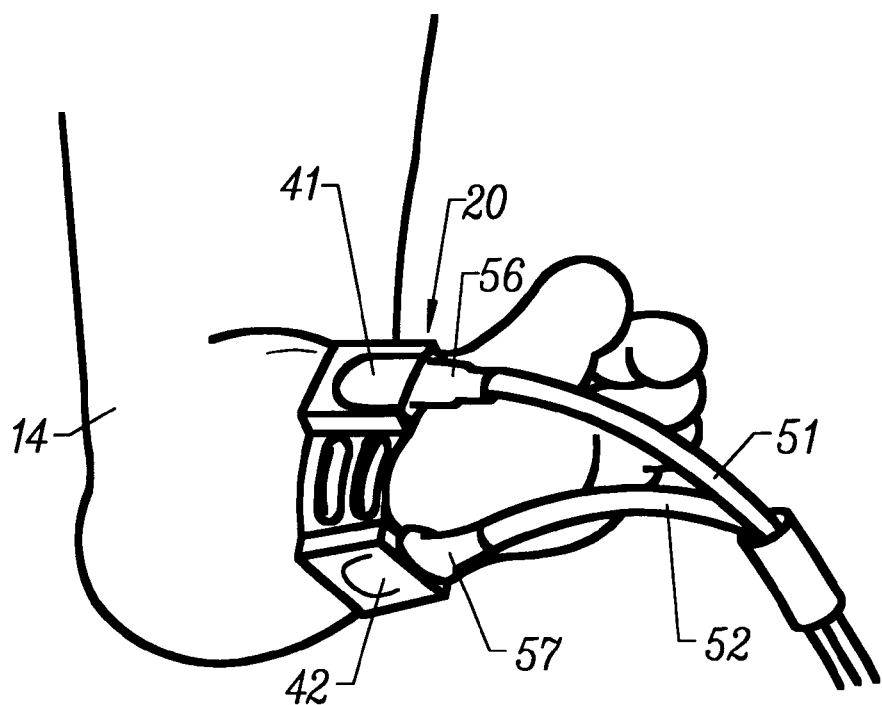
FIG. 3 is a perspective view showing the invention as applied to the left foot of an infant and showing the connecting cables running away from the patient's ankle.

FIGS. 1–3 show the pulse oximetry sensor 20 as applied to the left foot 12 of an infant patient. The connecting cables 51 and 52 extend away from the patient's ankle 14 and then are connected to an oximetry device known in the art. The present invention is limited to the sensor mechanisms (including the connector cables) and the foot wrap for holding the sensors on the patient's foot without requiring adhesive. As shown best in FIG. 2, the foot wrap means 30 is wrapped around the patient's foot 12. The sensor receptacles 41 and 42 are positioned adjacent the medial (great toe) side 13 of the patient's foot 12. A slide means 60 carries a plunger means 70 having a handle 71 carrying a piercing member 72. The slide means 60 is used to adjust and lock the foot wrap 30 on the patient's foot. When the foot wrap 30 is snug, as shown in FIG. 2, the plunger means 70 is depressed by pushing down on handle 71 which drives piercing member 72 through foot wrap 30, holding resilient foot wrap 30) securely in position (without restricting circulation) on the. infant's foot. The receptacles 41 and 42 are properly placed to receive the sensors 56 and 57 carried at the ends of cables 51 and 52, respectively.

Figure 4:
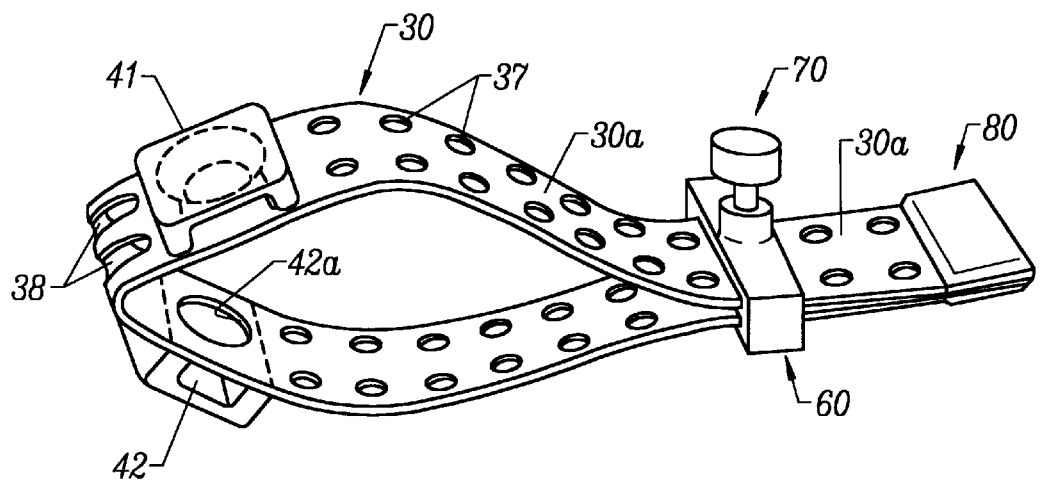
FIG. 4 is a perspective view of the foot wrap.
Figure 5:
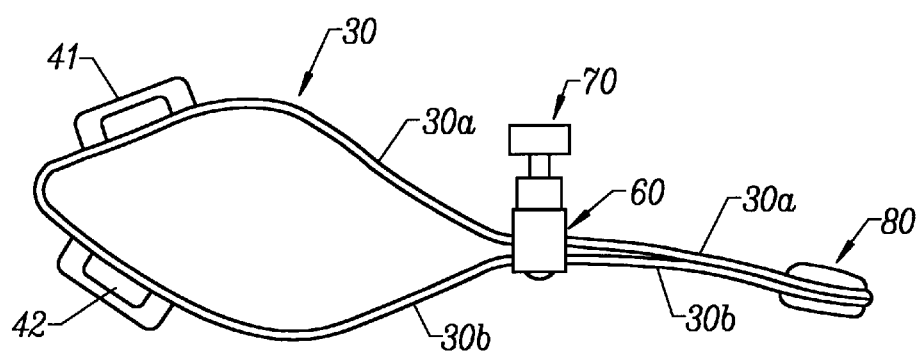
FIG. 5 is a side elevational view showing the foot wrap.
Figure 8:
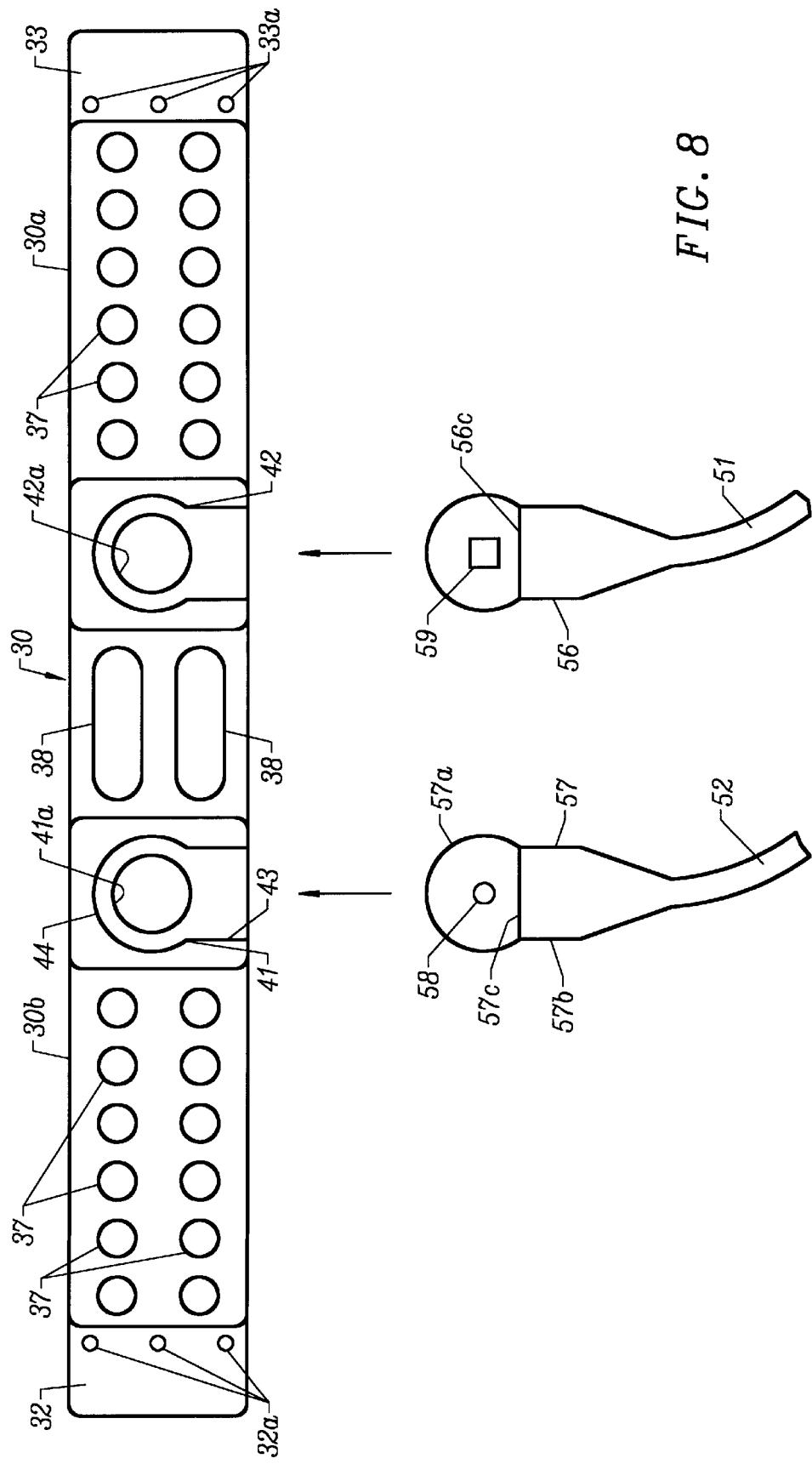
FIG. 8 is a schematic representation of the foot wrap laid flat showing that the shape of the emitter and photodetectors match the shape of the receptacles.
Figure 9:
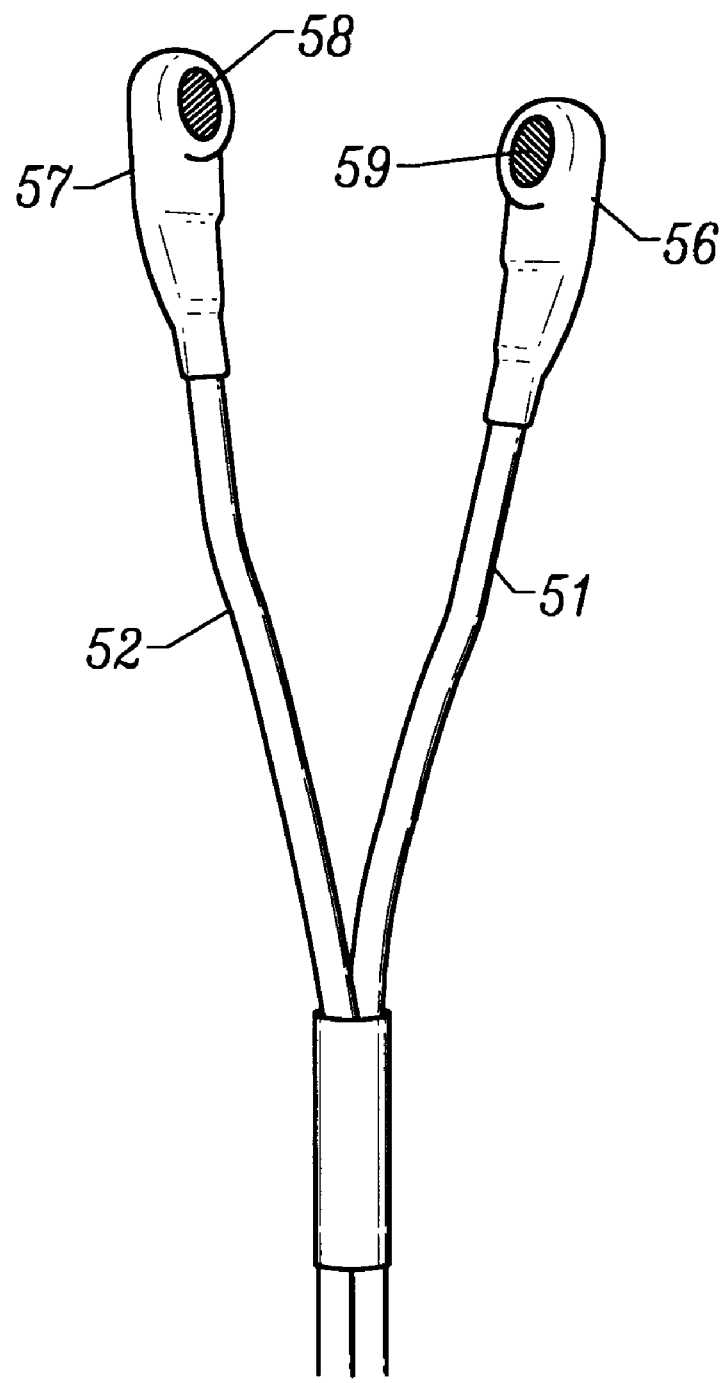
FIG. 9 is a perspective view of the cable and sensor heads.

FIGS. 4, 5 and 8 show resilient foot wrap 30, which is preferably made of resilient and thin rubberlike material such as Kraton. The material is formed into an elongated band having first and second ends 30a and 30b. First and second ends are positioned so that they extend parallel to each other and adjacent each other in the teardrop shape shown in FIGS. 4 and 5 to be inserted into slide 60. Near the center portion of the flexible band, receptacles 41 and 42 are formed during the process of injection molding. Each receptacle 41 and 42 forms a "pop-in" socket which encircles and grips a sensor. Each receptacle 41,42 has a circular opening 41a,42a formed therein to allow the passage of light from emitters 58 to photodetector 59. Foot wrap 30 has a first portion 30a which extends across the top of the baby's foot, as shown in FIGS. 3–5, and a second portion 30b which extends underneath the baby's foot.

In the preferred embodiment, the entryway 43 of receptacle 41 has a width which is slightly less than the width of the sensor head 57a so that the sensor head must be pushed with sufficient force into the entryway 43 of receptacle 41 to stretch the resilient material. When the sensor head reaches the end 44 of receptacle 41, the neck 43 of the receptacle pops onto the reduced neck portion 57b of the sensor 57 and resiliently grips and surrounds the sensor 56 as shown best in FIG. 3. The sensors must be held securely in position relative to each other and relative to the patient's foot to obtain consistent and reliable oximetry readings. As shown in FIG. 8, sensor 57 carries emitters 58 and sensor 56 carries photodetector 59. Sensor 56 is sized to "pop-in" to receptacle 42 in the same manner as sensor 57 and receptacle 41.

The resilient and elongated band 30 has a plurality of openings or holes 37 formed therein and a pair of somewhat larger openings or holes 38 formed between receptacles 41 and 42. The openings 37 and 38 allow the egress of perspiration from the infant's foot, which perspiration if allowed to collect under the rubber foot wrap might be injurious to the infant's skin. The plurality of holes also helps the wrap to grip the infant's foot with minimum pressure and with no significant adverse affect on circulation in the baby's foot. This is important so that the foot wrap may be applied to the foot and retained securely in position without the use of adhesives.

Figure 6:
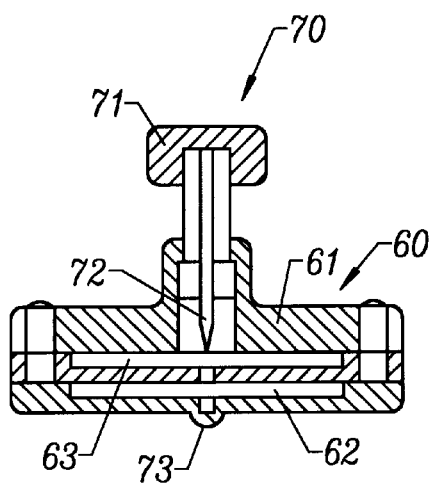
FIG. 6 is a sectional view showing the slide and plunger means used in conjunction with the foot wrap shown in FIG. 5.
Figure 7A:
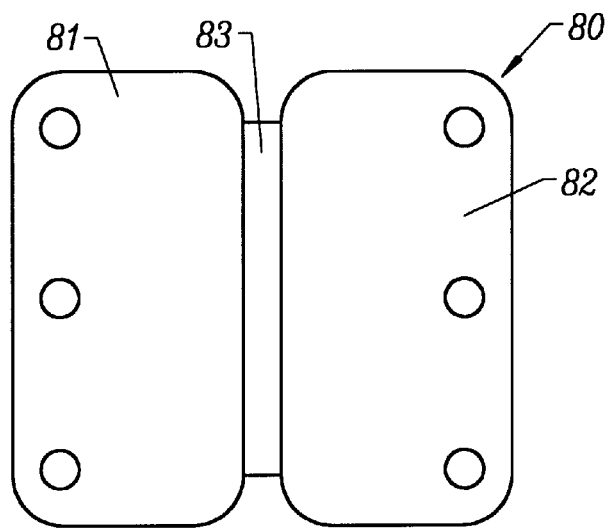
FIGS. 7A and 7B show the connector used to hold together the ends of the band shown in FIG. 5.
Figure 7B:
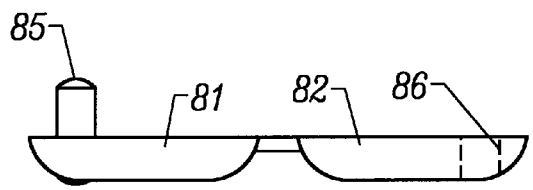

FIG. 6 shows the slide 60 and plunger means 70 used to tighten the foot wrap; the slide 60 and plunger means 70 together form an adjustment means as shown in FIGS. 1, 2, 4 and 5. The slide 60 includes a body portion 61 having two slotted openings 62 and 63 formed therein through which the first and second ends of band 30 are inserted so that slide 60 slidably receives ends 30a and 30b. After slide 60 has had the ends 30a and 30b slid through its slots 62 and 63, a retainer 80, shown in FIGS. 7A and 7B, is applied to the ends of band 30. Retainer 80 holds the first and second ends securely together and prevents slide 60 from moving off the band and becoming separated from it.

Retainer 80 includes first and second tabs 81 and 82 joined by a hinge section 83. Tab 81 carries preferably threes lugs 85 which are pressed into openings 86 carried by tab 82. Lugs 85 extend through holes 32a and holes 33a formed in the ends 32 and 33 of band 31, securely fastening those ends together.

Plunger means 70 includes a handle 71 and a piercing member 72 as well as a protective cover 73 formed on the lower side of slide body 61 to cover the point of the piercing member 72. The piercing member 72 pierces the resilient foot wrap portions 30a and 30b on either side of receptacles 41 and 42, as shown best in FIGS. 1 and 2. When the handle 71 is depressed and piercing member is driven through two portions 30a and 30b, the tightness of the resilient band around the piercing member 72 holds it in position and prevents slide 60 from moving. The resilient foot wrap is reusable many times and may be soaked in an antiseptic solution such as alcohol, or in detergent.

Conductive cables 51 and 52 are assembled with the emitters 58 and photodetector 59 and are coated by being dipped in white polyurethane rubber. After hardening of the rubber coating, a small disc of the coating is cut away over the emitting and sensing elements to allow for the passage of light.

What is claimed is:

1. A pulse oximetry sensor for use on pediatric patients, comprising:

a resilient foot wrap adapted to extend around and resiliently grasp the patient's foot, wherein said foot wrap is a band with first and second ends extending parallel and adjacent each other, adjustment means for tightening said foot wrap on said patient's foot, said adjustment means including a slide having slotted openings into which said first and second ends of said band are inserted, said slide being movable with respect to said first and second ends, and a plunger carried by said slide, said plunger having a handle and a piercing member connected to said handle, said plunger being movable between a first position in which said piercing member extends through said band and a second Position in which said piercing member is retracted and does not engage said band, first and second resilient receptacles carried by said foot wrap means, and a light emitter and photodetector removably carried by said first and second resilient receptacles, respectively, said receptacles each having an entryway, said light emitter and photodetector each having a larger size than said respective receptacle entryway, whereby said resilient receptacle entryways stretch as said light emitter and photodetector are inserted therein to grip and securely hold said light emitter and photodetector.

2. The apparatus of claim 1 further comprising a retainer for connecting said first and second ends of said band together.

3. A resilient foot wrap for use in conjunction with a pulse oximetry sensor for use on pediatric patients, said resilient foot wrap comprising:

an elongated, resilient band adapted to extend around the patient's foot, said band having first and second ends, a slide adapted to slidably receive said first and second ends of said band, said slide being movable with respect to said first and second ends, a plunger means carried by said slide for engaging said band, said plunger means having a piercing member movable between a first position in which said piercing member extends through and engages said band and a second position in which said piercing member is retracted and does not engage said band, and first and second receptacles carried by said band for carrying a light emitter and a photodetector, respectively.

4. The apparatus of claim 3, wherein said receptacles are resilient and have entryways, and wherein said light emitter and photodetector is each larger than its respective receptacle's entryway, so that each entryway stretches to grip and securely hold said light emitter and photodetector.

* * * * *